United States Patent [19]
Stern et al.

[11] Patent Number: 5,908,946
[45] Date of Patent: Jun. 1, 1999

[54] PROCESS FOR THE PRODUCTION OF ESTERS FROM VEGETABLE OILS OR ANIMAL OILS ALCOHOLS

[75] Inventors: Robert Stern, Paris; Gérard Hillion, Herblay; Jean-Jacques Rouxel, Vigny; Serge Leporq, Mantes La Ville, all of France

[73] Assignee: Institut Francais du Petrole, France

[21] Appl. No.: 08/908,983

[22] Filed: Aug. 8, 1997

[30] Foreign Application Priority Data

Aug. 8, 1996 [FR] France .................................. 96 10102

[51] Int. Cl.[6] .................................................. C07C 51/00
[52] U.S. Cl. ........................................... 554/167; 554/168
[58] Field of Search ..................... 554/167, 168

[56] References Cited

U.S. PATENT DOCUMENTS

| | | | |
|---|---|---|---|
| 581,897 | 5/1897 | Berger et al. | |
| 712,747 | 7/1902 | Schlüter ......................................... | 2/3 |
| 5,525,126 | 6/1996 | Basu et al. ................................ | 44/308 |
| 5,532,392 | 7/1996 | Gheorghiu ............................ | 554/169 |

FOREIGN PATENT DOCUMENTS 9721697 6/1997 Germany.

OTHER PUBLICATIONS

B. Screenivasan, "Interesterifcation of Fats", *J. of Amer. Oil. Chemists' Soc.*, vol. 55, pp. 796–805, 1978.
Patents Abstracts of Japan, vol. 013, No. 308 (C–617) Jul. 14, 1989 (JP 01093558).
J. Am. Oil Chem. Soc. (1984), 61 (10), pp. 1593–1597, Oct. 1984.
Cemical Abstract (CA: 106:140998), Oct. 1986.

*Primary Examiner*—Paul J. Killos
*Assistant Examiner*—J. Parsa
*Attorney, Agent, or Firm*—Millen, White, Zelano & Branigan P.C

[57] ABSTRACT

For the production of linear monocarboxylic acid esters with 6 to 26 carbon atoms vegetable oils or animal oils, which may or may not be neutral, are reacted with monoalcohols having a low molecular weight, for example 1 to 5 carbon atoms, in the presence of a catalyst that is selected from among zinc oxide, mixtures of zinc oxide and aluminum oxide, and the zinc aluminates that correspond to the formula:

$$ZnAl_2O_4, x\ ZnO, y\ Al_2O_3$$

(with x and y each being in the range of 0–2) and having more particularly a spinel type structure, thereby enabling the direct production in one or more stages, of an ester that can be used as a fuel or combustible and a pure glycerine.

21 Claims, No Drawings

PROCESS FOR THE PRODUCTION OF ESTERS FROM VEGETABLE OILS OR ANIMAL OILS ALCOHOLS

This invention relates to a new process for the production of monocarboxylic acid esters from vegetable oils or animal oils. It relates more particularly to the production of linear monocarboxylic acid esters with 6 to 26 carbon atoms, by reacting vegetable oils or animal oils, which may or may not be neutral, with monoalcohols, for example having low molecular weight, with 1 to 5 carbon atoms, or having higher molecular weight, in the presence of a catalyst that is selected from among zinc oxide, mixtures of zinc oxide and aluminum oxide, and the zinc aluminates that correspond to the formula $ZnAl_2O_4$, x ZnO, y $Al_2O_3$ (with x and y each being in the range of 0–2) and more particularly having a spinel type structure.

The reaction that is the principal objective is a transesterification that is achieved according to Reaction Scheme 1 below and optionally an esterification- and transesterification-linked reaction, with the esterification being carried out according to Reaction Scheme II below.

Reaction Scheme I 1 triglyceride+3 alcohols→6 3 esters of fatty substances+ glycerine.

Reaction Scheme II

Fatty acid+alcohol→6 fatty acid esters+water

Fatty acid+glycerine→6 glyceride+water

BACKGROUND OF THE INVENTION

The esters of fatty substances are currently used in many applications as diesel fuels, household fuels, ecological solvents, basic compounds for the production of sulfonates of fatty alcohols, amides, ester dimers, etc.

In the case of diesel fuel, which today constitutes a large application for esters of fatty substances, a certain number of quite varied specifications have been established. The ester should not contain heavy compounds (triglycerides), few diglycerides and sterol esters, few monoglycerides, for example, less than 5%, few free fatty acids that can be corrosive, and little free glycerine, for example less than 0.2%, no strong acid or metal traces at all. This means that there is a specific protocol for obtaining the desired purity.

In the case of household fuel, it is clear that all these specifications are not always useful and are even sometimes counter-productive, but with the market for household fuel and that for gas oil often being merged, the specifications for household fuel resemble those of gas oil because in France, for example, household fuel can be used in farm tractors and construction-site equipment.

When an ester is produced from oil and monoalcohol, it automatically forms, depending on the nature of the oil that is employed at the beginning, 10 to 15% of a secondary product, which is glycerine. This glycerine is sold at a high price for varied purposes, but only when it is of high purity. The latter is obtained after purification steps that are carried out in specialized vacuum distillation units.

In short, most of the commercial processes for producing esters lead quite readily to raw products (esters and glycerine) which, however, have to be purified extensively by various treatments which ultimately raise the cost of the transformation.

Also, in the production of methyl esters of fatty substances from refined oils and dry alcohol, while simple alkaline derivatives, such as sodium, soda, or potassium alcoholates, are now used as catalysts, under rather mild conditions (temperature of 50 to 80° C. and atmospheric pressure), as indicated in numerous patents or publications, for example, in JAOCS 61, 343–348 (1984), a pure product that can be used as fuel and a glycerine within specification can be obtained only after numerous stages.

If, for example, the most widely used alkaline catalysts are considered, traces of alkaline compounds are found both in the glycerine and in the ester, and it is necessary to remove them by washing the ester fraction and drying it. In the glycerine phase, it is necessary to neutralize the soaps and the alcoholates that are present, filter the salts that are formed, evaporate the glycerine after having eliminated the water, barring running the diluted glycerine over ion-exchange resins, before the salt-free glycerine is concentrated. Finally, it is always necessary to evaporate excess alcohol and often to distill it to keep this evaporation, mainly when it is carried out in the ester phase, from causing the ester that is present to react with the partially dissolved glycerine, which would lead to the formation of monoglycerides.

In short, to achieve the specifications that are desired for the glycerine and the ester, it is necessary to resort to so many stages that only large scale operation are economically viable.

SUMMARY OF THE INVENTION

It has now been surprisingly discovered, that it was possible to obtain in 1 to 3 stages, particularly under preferred conditions, directly from vegetable oils or animal oils and monoalcohols, fairly pure esters and a colorless and sometimes odorless glycerine by using as catalysts, either continuously, for example, in a fixed bed, or discontinuously, a catalytic system with a zinc oxide base, which may or may not be deposited on an alumina. The catalysts are either zinc oxide or a mixture of zinc oxide and aluminum oxide, or a zinc aluminate that is preferably defined by a certain structure, for example spinel, and which corresponds to the formula ZnAl2O4, x ZnO, y Al2O3 (with x and y each being in the range of 0–2).

All these catalysts are either in the form of a powder, of balls, extrudates, or pellets; zinc oxide used by itself is a catalyst. The use of alumina has two favorable effects, however. The first is often to increase the surface area; the second is to create a much more stable compound, mainly with regard to conditions under which the zinc compound would have a tendency to form zinc soaps.

Another advantage of zinc oxide-based catalysts is their ability to catalyze the transesterification of the oil with heavier alcohols than methanol. Thus, it is possible to form ethyl esters, isopropyl esters, or butyl esters, which have an advantage in the domain of fuels because often the pour points of the esters that are formed with these alcohols are lower than those of the methyl esters, with the gain sometimes being 10° C., which makes it possible to use more saturated oils from the outset.

Generally, in the conventional processes that use alkaline catalysts, a single phase between the heavy alcohols, ester, and glycerine is formed after the reaction, so that it is not possible to easily decant the glycerine and thus to obtain good conversion in a single stage. In this case, the process is complex. Not only is it necessary to ensure an intermediate decanting of the glycerine with evaporation of the alcohol, but also to purify the ester and the final glycerine.

In comparison, less steps are generally required by using heterogeneous zinc catalysts. In the process of this invention, a two-stage reaction is often employed; in the first, the ester and the glycerine are decanted when the conversion reaches at least 80%, after the excess alcohol is eliminated. In a second stage, a quantitative yield is obtained by adding the necessary alcohol and by setting optimum conditions. It is also possible to obtain these heavy esters, however, in a single stage with 90% conversion rates and to subject the ester to vacuum distillation after having eliminated the alcohol and the glycerine. It is also possible to produce directly any ester with a high content of monoglyceride, which can be advantageous in certain applications.

FURTHER BACKGROUND OF THE INVENTION

The use of heterogeneous catalysts is in general not new. However, it does not seem possible in any industrial process to obtain both the ester and glycerine economically. Producing economically means obtaining an ester within specification and a pure glycerine, at a reasonable spatial velocity and reaction times, and without a rigorous purification system.

Among the prior documents that deal with heterogeneous catalysts, it is possible to cite European Patent EP-B-0 198 243. The transesterification catalyst, which transforms oil and methanol into methyl ester, is an alumina or a mixture of alumina and ferrous oxide. In the examples, the column that is used for the fixed bed has a volume of 10 liters, and oil is generally injected at a flow rate of less than 1 liter/hour, which gives a VVH (VVH=volume of injected oil/volume of catalyst/hour) of less than 0.1. For a factory of 100,000 t/year, this would correspond to reactors of at least 150 m$^3$.

Another problem which seems to arise is that of the amount of glycerine that is collected, which is far less than the theoretical value. In no example where 10% glycerine is supposed to be collected is anything even approaching this value obtained. Finally, the purity of the esters is fairly low, from 93.5 to 98%. What becomes of the glycerine that is not recovered is not indicated. In some cases, it forms glycerine ethers, such as the one that is indicated in this patent; in other cases, it may breakdown, unless it is eliminated in a first stage. The performance level is therefore quite low. It is possible to point out that with the VVH indicated and for contact times of more than 6 hours, conversions of 80% and more can be obtained even without a catalyst.

This European patent therefore does not appear to offer a reasonable solution from an economic standpoint.

English Patent GB-A-795 573 describes using a zinc silicate as a catalyst at temperatures of between 250 and 280° C. and under a pressure of at least 100 bar, with methanol. It appears that there was 85% conversion in a first stage and 100% if the glycerine was decanted in an intermediate step and the reaction was continued. According to patent EP-B-0 193 243, which cites GB-A 795 573, zinc soaps would be formed with the zinc compounds, which naturally cannot be allowed in fuels. This is mainly due, it seems, to the high temperatures that it is necessary to use in this reaction with this catalyst.

In the first stage of the process that is described in this patent, or in the second stage if there are two transesterification stages, the glycerine is diluted, and the ester is washed. In this process, there are therefore the following potential drawbacks:

High pressure, more than 100 bar,
high temperature, 250 to 280° C.,
washing the phases with water and necessary purification of the glycerine, need, in order to recycle the methanol, to distill it and not evaporate it.

In addition, the U.S. Pat. No. 4,668,439 is known, which describes a continuous production process in which operations are carried out at atmospheric pressure and where the ester and the glycerine are evaporated by running excess alcohol through oil at more than 210° C., most often at 240° C., in the presence of a soluble catalyst, which can be a zinc laurate. The only example of a zinc compound that is given in this document is, for that matter, the laurate; otherwise, the compounds are alkalis and various soaps. All the examples use soluble catalysts. Glycerine represents only 70% of the theoretical value, which means that there are either losses or decomposition. In this process, the ester and the glycerine are evaporated by the passage of alcohol, which also raises the possibility of only the ester evaporated and not the monoglycerides, whose boiling point is close. From the energy standpoint in particular, the effectiveness of this process is questionable.

There are other references in the literature that do mention zinc oxide, but in esterification reactions of glycerine with a fatty acid [Osman in "Fette Seifen und Anstrichmittel [Fats, Soaps, and Coating Media]" 331–33 (1968)]. In this work, about 20 catalysts are compared at 180° C. in a discontinuous process. There is virtually no difference between zinc chloride, zinc sulfate, zinc powder, barium oxide, calcium oxide, zinc oxide, alumina, thiosalicylic acid, calcium phosphate, potassium bicarbonate, sodium methylate or sodium ethylate, and even lithium hydroxide. All these salts or oxides provide yields of between 32 and 39% of monoglyceride in a comparative test where excess glycerine is used relative to the fatty acid.

The fatty acid+glycerine reaction is the one described in Reaction Scheme II where, instead of having a neutral oil at the start, there is an acidic oil. This is therefore a first stage whose purpose is to eliminate the acidity of the oil. This reaction is fairly easy because it involves only several percent of the main reaction. In this connection, the use of zinc aluminate is not considered preferable to zinc in the list of catalysts if it is desired to avoid saponification and/or the formation of zinc salts. Esterification is an easier reaction than transesterification because there is elimination of a reagent; this did not taken place in high-temperature transesterification, where the glycerine remains present and soluble.

Finally, the prior art does not provide information on a reaction that can be employed economically on a industrial scale in producing esters by transesterification.

DETAILS OF THE INVENTION

This invention therefore proposes a process for the production of at least one fatty acid ester and glycerine, with these two products being obtained with a high degree of purity. This process can be defined in a general manner by the fact that the operation is carried out starting with various alcohols of C1 to C18 and varied oils, vegetable or animal, acid or neutral, by using at least one catalyst that is selected from among zinc oxide, mixtures of zinc oxide and aluminum oxide, and zinc aluminates that are defined by a certain structure, for example of the spinel type, and that corresponds to the formula $ZnAl_2O_4$, x ZnO, y $Al_2O_3$ (with x and y each being in the range of 0–2), under conditions that preferably include a temperature of between 170 and 250° C. and a pressure that is less than 100 bar and preferably 10 to 60 bar.

By using this process, final purification is reduced to a minimum, while making it possible to obtain an ester and a glycerine within specifications.

Among the oils that can be used in the process of the invention, included, but limited thereto are the currently available oils, such as palm oils, cabbage palm oils, coconut oils, babassu oils, old or new colza oils, sunflower seed oils, corn oils, cottonseed oils, tallow, lard, peanut oils, linseed oils, and cramble oils and all the oils that come from, for example, sunflower seeds or colza by genetic engineering or hybridization.

It is even possible to use frying oils, squaring oils, various animal oils, such as fish oils, and even fats because more than 10° C. in pour point can be gained with the esters that are formed with certain alcohols.

Among the oils that are used, it is also possible to mention oils that are partially modified by, for example, polymerization or oligomerization.

The presence of fatty acid in the oils is not detrimental a priori; otherwise there is the danger of saponification. For the acidic oils, it is therefore preferable to have the transesterification reaction preceded by an esterification reaction, preferably with glycerine, to form a glyceride from fatty acids, at atmospheric pressure or under a partial vacuum and at temperatures of 180 to 220° C.

The nature of the alcohol that is used in the process of the invention plays an important part in the activity of the transesterification. In general, it is possible to use various aliphatic monoalcohols that contain, for example, 1 to 18 carbon atoms. The most active is methyl alcohol. However, ethyl alcohol and isopropyl alcohols, propyl alcohols, butyl alcohols, isobutyl alcohols, and even amyl alcohols can be employed. It is also possible to use heavier alcohols such as ethyl-hexyl alcohol or lauryl alcohol. It is also possible advantageously to add methyl alcohol, which seems to facilitate the reaction, to the heavy alcohols. Further, when ethyl ester is prepared, it is possible to use 1 to 50%, preferably 1 to 10%, methyl alcohol to increase the conversion.

The catalyst that is used can be obtained by one of the following procedures:

1. Impregnating at least one soluble zinc salt of alumina balls, drying, then calcination.
2. Mixing of at least one zinc compound and hydrated alumina in the presence of a peptizing agent (nitric acid, acetic acid). The zinc compounds are then selected from the group that is formed by zinc oxide, zinc hydroxide, zinc carbonate, and zinc hydroxycarbonate. The mixed product is then shaped by extrusion, and then dried and calcined.
3. Coprecipitation which involves, on the one hand, an aqueous solution of soluble salts of zinc and optionally aluminum (nitrates, sulfates, acetates, etc.) and, on the other hand, an aqueous solution of sodium carbonate or sodium bicarbonate or sodium aluminate. The aluminum is therefore present in cationic form $Al_3+$ and/or anionic form $AlO_2^-$. The coprecipitation is brought to a constant pH (between 6 and 8) as is known to one skilled in the art, then the coprecipitate is carefully washed to limit the residual sodium content to less than 0.5%, and preferably less than 0.1% by weight relative to the oxides. In an advantageous way, the coprecipitate is crystallized in the form of hydroxycarbonate with a hydrotalcite structure. The washed coprecipitate is dried, then activated thermally and shaped by extrusion as above, or else shaped by pelletizing. The spinel phase is formed during thermal activation (for example at 400° C. for 2 hours) by decomposition of the hydrotalcite phase.

Regardless of the preparation method adopted, it is preferable that at least 10% of the ZnO, preferably 20%, and even more preferably at least 30% of ZnO, be combined with the alumina in the zinc aluminate form. The proportion of zinc aluminate is determined by X-ray diffraction as is known to one skilled in the art.

It is important to eliminate the alkaline salts before calcining them because otherwise the real catalyst would, in fact, be the alkaline impurity, which would dissolve slowly in the medium, and, in this case, catalytic activity would gradually decrease.

It may be advantageous to calcine the catalyst at a sufficient temperature to combine the alumina and zinc oxide and to obtain the spinel phase $ZnAl_2O_4$, x ZnO, y $Al_2O_3$ (with x and y each being between 0 and 2). A temperature of at least 400° C. for at least two hours is recommended.

Finally, it is important not to reduce the surface area and the pore volume of alumina or zinc excessively or carelessly. In general, the catalyst has a surface area of 10 to 200 $m^2/g$ and a pore volume of 0.2 to 1.2 $cm^3/g$, preferably a surface area of between 50 and 200 $m^2/g$ and a pore volume that is greater than 0.3 $cm^3/g$. Finally, there is an advantage in having a pore distribution of between 0.01 and 0.1 micron.

If the transesterification is carried out in the absence of catalyst, either in an autoclave, or in a fixed bed with inert carriers, such as silicon carbide, it is possible to obtain, at certain temperatures, conversions which exceed 80%, but at very low VVH and with very long residence times. A thermal reaction therefore exists, and it is sometimes difficult to distinguish between the catalytic effect and the thermal effect; this accounts for the fact that with simple aluminas, high conversion rates can be obtained. However, the object of the process of the invention is to obtain these conversion rates with reasonable residence times, i.e., with reasonable VVH.

The operating conditions that are used clearly depend on the process that is selected. If a discontinuous reaction is used, it is possible to work in one or two stages, i.e., to achieve a first reaction with 85–90% conversion, to cool excess methanol by evaporation, to decant the glycerine, and to finish the reaction by again reheating and adding alcohol to achieve total conversion. It is also possible to aim for a conversion rate of 98% by working for a sufficiently long time in a single stage.

If a continuous reaction is undertaken, the operation can be performed with several autoclaves and decanters. In the first reactor, a conversion of, e.g., 85% is achieved; in a second reactor, decanting is done by evaporating the alcohol and by cooling. In a third, the transesterification reaction is accomplished by adding a portion of the alcohol that was evaporated previously. Finally, excess alcohol is evaporated in an evaporator, and the glycerine and esters are decanted.

If a continuous process in a fixed bed is selected, it is possible to work advantageously at temperatures of 210 to 250° C., preferably 230 to 240° C., at pressures of 30 to 50 bar, if the methyl esters are produced, with the VVH preferably being between 0.3 and 3, preferably 0.5 to 2, in the first stage and with the alcohol/oil weight ratio varying from 2/1 to 0.1/1.

The introduction of the alcohol can be advantageously conducted in fractions. Introduction into the tubular reactor at two levels can be done in the following way: supplying the reactor with oil and about ⅔ of the alcohol that is to be used, then introducing the alcohol supplement approximately at the level of the upper ⅓ of the catalytic bed.

If 250° C. is not exceeded, an ester of the same color as the starting oil and a colorless glycerine are generally obtained after decanting. The ester can be run over a resin, an adsorbent earth (more particularly, a clay activated by treatment with a strong acid) and/or activated carbon, the same as with glycerine. It is possible to reduce the monoglyceride content of the ester by washing with glycerine in the presence of alcohol, for example methanol.

The presence of water in the reaction is harmful because it promotes the formation of fatty acids, i.e., of reagents that may well react with the catalyst to form soaps.

The analysis of the compounds that are produced is done either by chromatography of the gaseous phase for esters and glycerine or, more quickly, by liquid exclusion chromatography for esters. It is noted that the process of the invention, unlike known processes that are carried out with basic catalysis with alcohols, produce very little or nothing in the way of sterol esters. The sterol esters, which are heavy products, can cause deposits at the edges in the injectors.

If it is desired to obtain a very pure ester, it is not impossible, even if this is not the main object of the invention, to provide a system to include the following stages:

discontinuous or continuous transesterification of the oil on a fixed bed or in an autoclave, with at least 80–85% or, preferably, at least 90–95% conversion, the evaporation of excess monoalcohol;

the decanting of the glycerine and the ester, with said ester being recycled in a second stage to undergo transesterification with a portion of the monoalcohol that is recovered in the first evaporation;

then re-evaporation of the excess monoalcohol in the second transesterification step, the decanting under ambient conditions, and the separation of the glycerine and the ester.

This system is supposed to compete with a system that would use two transesterifications or one transesterification but with fairly long periods. It makes it possible to obtain in four stages a pure ester and a pure glycerine.

The examples that are presented below do not limit the invention and are used only to illustrate it.

EXAMPLE 1

Into a 500 cm3 autoclave that is equipped with an effective stirring mechanism, 120 g of refined colza oil, 120 g of methanol, and 1.2 g of zinc oxide powder whose surface area is 160 m2/g are introduced under ambient conditions. Heating is done with an electric heater to achieve 225–230° C. in the autoclave. The pressure rises to 44 bar. Samples are taken after 2 hours and 6 hours. The conversion rate into esters is respectively 88 and 92.7% by weight.

Under the same conditions, the same recycled catalyst yields 91.1 and 94.3% after 2 hours.

This catalyst is heated to 210–220° C. in the presence of 260 g of methanol only. On the order of 1000 ppm of water is formed after 5½ hours, which shows that with zinc at these temperatures, dimethyl ether does not form.

EXAMPLE 2

Influence of Water

The preceding catalyst, which had been treated with methanol at 210° C., was reused at 220–230° C. With 1.5 g of catalyst, 120 g of oil, 120 g of methyl alcohol, and 3 g of water, 93.2% of ester is obtained after 2 hours, and 94.1% of ester is obtained after 5 hours. The pressure under the hot operating conditions was 43 bar. It is therefore noted that there is no deactivation of the catalyst after 3 passages. In fact, on a consistent basis fairly high stability of the catalyst is noted, in particular when a zinc aluminate is used.

EXAMPLE 3

Influence of the Temperature 1.8 g of the catalyst of Example 1 is mixed with 180 g of refined colza oil and 60 g of methanol. The conditions of the reaction are fairly mild; a temperature of 170–175° C. and a pressure of 10 to 14 bar. After 2 hours, 59.4% of ester is obtained, and 64% of ester is obtained after 4 hours. The calculated temperature that corresponds to the established pressure is actually 137 to 153° C., but the calculation does not take into account the presence of the oil of the ester and the glyceride chemicals, which reduce the vapor pressure of the methanol.

EXAMPLE 4

Without catalyst, oil and alcohol are introduced under the conditions that are listed in Table 1 below, in the apparatus of Example 1. All the % are expressed by weight.

TABLE 1

| Oil (g) | Methanol (g) | Water (g) | T (° C.) | Ester 2 hours (%) | Ester 6 hours (%) |
|---|---|---|---|---|---|
| 120 | 120 | — | 227 | 57 | 75.6 |
| 120 | 120 | — | 227 | 61 | 73.7 |
| 120 | 120 | 3 | 227 | 28.3 | 56.2 |
| 120* | 120 | — | 224–6 | 91 | 94.3 |

*with 1.2 g of zincoxide

It is noted here that in the absence of water, after only 2hours nearly 60% of ester is obtained without catalyst, but 91% in the presence of zinc oxide.

EXAMPLE 5

A transesterification that may or may not be in the presence of catalyst is carried out under fairly advantageous conditions from the economic standpoint because there is little methanol to be recycled. The following results are obtained which show the effect of the catalyst.

TABLE 2

| Oil (g) | Methanol (g) | Catalyst (g) | T (° C.) | Ester after 4 hours (%) |
|---|---|---|---|---|
| 180 | 60 | — | 227 | 37 |
| 180 | 60 | 1.8 ZnO/Al$_2$O$_3$ | 227 | 74.2 |

EXAMPLE 6

A carrier is employed based on alumina balls having starting surface area of 146 m$^2$ and a pore volume of 1.1 cm3/g. The alumina impurities are mainly 400 to 1000 ppm of sodium and less than 1000 ppm of calcium, magnesium, silicon, and iron. The balls have a diameter of 1.6 to 3 mm.

The alumina balls are impregnated with zinc nitrate, then subjected to calcination at 500° C. These operations are repeated several times. Thus, a catalyst that contains 29% of zinc is produced. The catalyst obtained has the following characteristics:

Surface area: 65 m²
Pore volume: 0.63 cm³/g
  dimensions of pores: 0.07 micron to 10 microns
  pores of less than 0.1 micron: 55% by volume
  pores of less than 1 micron: 65% by volume
  pores of less than 10 microns: 100% by volume A certain heterogeneity therefore characterizes this catalyst.

The substrates that are used are the refined colza oil whose acid number is less than 1 and methanol that contains less than 0.3% of water.

Methanolysis or ethanolysis is carried out in a device that comprises a fixed bed reactor, i.e., a packed column having a diameter of 1.9 cm and a length of 120 cm, heated by 3 jackets which surround the column. The preheating of the oil and the methanol is done in the column on 10 cm3 of glass balls, and the reaction is carried out on a catalyst volume of 70 cm3. At the outlet of the column, 20 cm3 of tungsten carbide and 5 cm3 of glass balls were added. The device, which is in the shape of an inverted U, consists of a tubular reactor, cooling on the horizontal part, and a decanter, which constitutes the second branch. On the upper portion of the decanter, a gas-purging system makes it possible to regulate the pressure, i.e., initially to hold the pressure with nitrogen at the desired pressure of 15 to 60 bat. The decanter has a liquid purge at its lower outlet. When the decanter is half full, an automatic valve opens to partially empty the product obtained. At the flow rates selected and at a constant pressure, two pumps inject the alcohol and the oil upwardly into the column.

The reaction products are those that are collected after 24 hours of passage at the desired VVH (VVH=oil volume/catalyst volume/hour). The precaution of emptying the contents of the decanter completely before proceeding to a new test is often taken, however.

After having drawn off the feedstocks that contain methanol, glycerine and ester, generally present in a single phase, the feedstock that is produced over a period of 24 hours is evaporated in a rotary evaporator. The ester is decanted without washing the latter. The analysis of the ester is done by gel permeation chromatography (GPC in English).

The results are therefore those that are obtained without any final purification, unless said final purification consists in evaporating excess methanol and separating the ester from the glycerine by decanting, preferably at around 50° C.

The following tables present the results that are obtained either with a single carrier (Table 3) or with a carrier that is impregnated with zinc (Table 4).

The temperatures are precise within ±2° C. The VVH is the volume of oil that is injected per volume of catalyst and per hour. Ratio R is the ratio by volume of oil/alcohol, designated H/A. The stoichiometric ratio is theoretically 8. An oil/methanol ratio of 2 is therefore 4 times greater than stoichiometry. The pressure is the pressure that prevails in the decanter, expressed in bar.

The composition of the mixture is expressed by % by weight. It would be more correct to express it in mole %. It is noted by carrying out 20 or so sample calculations that for each percent of ester, this changes little. The difference between the molar % and the % by weight is 1% associated with molar %, if an oil is considered as a molecule that has 3 ester groups, a diglyceride, 2 ester groups and a monoglyceride, and 1 ester group. This shows that it is possible to maintain the % by weight.

The contact time takes into account the presence of methanol; it is determined by the equation:

$$\text{contact time} = \frac{70\,cm^3 \text{ of catalyst} \times 60(*)}{\text{volume by } cm^3 \text{ of oil} + \text{injected alcohol in 1 hour}}$$

(*)60=time in minutes.

In Tables 3 and 4 below:
E=esters
MG=monoglyceride
DG=diglyceride which does not contain sterol esters because they do not form under these conditions
TG=triglyceride

TABLE 3

Methanolysis of Colza Oil with the Carrier by Itself

| T (° C.) | VVH | R H/A vol/vol | P (bar) | TG (%) | DG (%) | MG (%) | E (%) | t de contact (min) |
|---|---|---|---|---|---|---|---|---|
| 230 | 1.0 | 1 | 50 | 41.9 | 16.7 | 5.6 | 35.5 | 30 |
| 240 | 0.5 | 2 | 50 | 19.9 | 9.6 | 5.9 | 64.5 | 40 |
| 230 | 0.5 | 1 | 50 | 28.3 | 13.1 | 5.95 | 52.6 | 60 |
| 230 | 0.25 | 0.5 | 50 | 23.3 | 12.0 | 5.6 | 59 | 80 |
| 240 | 0.125 | 0.5 | 50 | 2.8 | 2.8 | 3.3 | 91 | 160 |
| 240 | 0.125 | 2 | 50 | 2.1 | 3.0 | 4.5 | 90 | 350 |
| 240 | 0.062 | 0.5 | 50 | 0.8 | 1.7 | 2.4 | 95.1 | 350 |
| 240 | 0.062 | 1 | 50 | 0.03 | 1.5 | 2.8 | 95.3 | 480 |

[Key:]
t de contact (min) = contact time (min)

This table provides the results that are obtained each time after 24 hours of reaction.

TABLE 4

Methanolysis of Colza Oil with the ZnO Catalyst + Preceding Carrier

| T (° C.) | VVH | R H/A vol/vol | P (bar) | TG (%) | DG (%) | MG (%) | E (%) | t de contact (min) |
|---|---|---|---|---|---|---|---|---|
| 230 | 1 | 3.3 | 50 | 16.7 | 10.4 | 12.7 | 59.8 | 46 |
| 235 | 1 | 3.3 | 50 | 13.4 | 9.1 | 12.1 | 64.8 | 46 |
| 230 | 2 | 0.5 | 60 | 12.8 | 10.4 | 9.3 | 67.4 | 20 |
| 235 | 0.5 | 0.5 | 50 | 4.6 | 4.0 | 11.2 | 80 | 80 |
| 235 | 1.0 | 0.5 | 60 | 3.4 | 3.6 | 8.1 | 84.7 | 40 |
| 240 | 1 | 0.5 | 60 | 1.5 | 2.0 | 8.9 | 89.4 | 40 |
| 230 | 2 | 2 | 50 | 6.6 | 5.7 | 6.1 | 81.2 | 20 |
| 210 | 0.5 | 2 | 50 | 7.78 | 5.20 | 8.9 | 78.1 | 80 |
| 210 | 1.0 | 2 | 50 | 4.3 | 4.4 | 7.1 | 84 | 40 |
| 220 | 1 | 2 | 50 | 2.3 | 3.1 | 7.1 | 87.2 | 40 |
| 230 | 1 | 2 | 50 | 1.15 | 2.4 | 8.8 | 89.5 | 40 |
| 235 | 1 | 2 | 50 | 0.88 | 2.2 | 8.8 | 89.9 | 40 |
| 240 | 1 | 2 | 50 | 0.8 | 2.4 | 7.8 | 88.9 | 40 |
| 240 | 2 | 2 | 50 | 4.7 | 4.5 | 5.6 | 85 | 20 |
| 230 | 1 | 2 | 60 | 5.9 | 5.0 | 9.3 | 79 | 40 |
| 230 | 2 | 2 | 60 | 12.8 | 10.4 | 9.3 | 67.4 | 20 |
| 235 | 0.5 | 1 | 50 | 0.3 | 1.25 | 4.0 | 94.4 | 60 |
| 235 | 0.5 | 1 | 50 | 0.02 | 0.1 | 3.9 | 95.8 | 60 |
| 235 | 0.5 | 1 | 50 | 0.03 | 0.96 | 3.4 | 95.5 | 60 |
| 235 | 0.5 | 1 | 50 | 0.02 | 0.88 | 3.9 | 95.1 | 60 |
| 240 | 0.5 | 1 | 50 | 0.08 | 1.15 | 5.04 | 93.5 | 60 |
| 240 | 0.5 | 1 | 50 | 0.09 | 1.53 | 5.5 | 92.5 | 60 |
| 245 | 0.5 | 1 | 50 | 0.10 | 1.34 | 6.0 | 92.4 | 60 |
| 260 | 0.5 | 1 | 50 | 0.07 | 1.30 | 6.9 | 91.4 | 60 |

[Key:]
t de contact (min) = contact time (min)

It is noted from these two tables that to obtain 95% conversion into ester, a VVH of 0.062 for oil and a residence time of 350 minutes are required, with alumina balls. To obtain the same conversion, a VVH of 0.5 and a residence time of 60 minutes are required with the zinc compound. To obtain 85% conversion, which is adequate for the first stage, it is possible to operate with VVH=2, t=20 minutes, while with the alumina balls, 89% with VVH=0.125, t=350 minutes, is obtained. It is noted that the zinc aluminate makes it possible to obtain a remarkable degree of stability. Tests that are carried out after more than a month indicated the same conversion as at the beginning.

The effect of temperature is fairly moderate from 210 to 240° C., with the optimum being located between 230 and 240° C. Pressure seems to impart a negative influence between 50 and 60 bar, which may be explained by the fact that the higher the pressure above the bubble point, the less agitation there is because there is no longer a gaseous phase. The high ratio of alcohol relative to oil is rather favorable in theory, but excess alcohol also reduces contact time. There is therefore an optimum ratio, but it also depends on temperature and VVH. The pressure in the reactor also plays a role, but up to an optimum value.

A zinc analysis was carried out on about 10 samples obtained under different operating conditions between 230 and 260° C. The analysis was carried out by X-ray fluorescence, both on the ester and on the glycerine, which are obtained directly by simple evaporation of methanol, and decanting and separation of the two phases.

The single sample that contains zinc is a sample of glycerine that is obtained after a test that is carried out at 260° C. In this case, the zinc content rose to 60 ppm. In all the other samples, the zinc content was below the detection limit, which is 5 ppm.

EXAMPLE 7

A catalyst is produced by mixing an alumina gel and zinc oxide in the presence of a peptizing agent. More specifically, the catalyst was made from 63.8 g of ZnO and 136.2 g of alumina. After calcination, a portion of ZnO and a portion of alumina are intermingled in the zinc aluminate $ZnAl_2O_4$ being 12.70%, 43.92% and 43.38%, with respect to the total weight of the catalyst. By calculation, the values found for x and y in the formula $ZnAl_2O_4$, x ZnO and y $Al_2O_3$ are:

x=0.66 y−1.81

The catalyst that is obtained after calcination at 600° C. contains 25.6% zinc. The surface area is 132 m2/g for a pore volume of 0.509 cm3/g. 75% of the volume is occupied by pores having a diameter of less than 0.1 micron. 80% of the total surface area consists of pores of less than 0.01 micron, and the other 19% consists of pores of 0.01 to 0.1 micron. The results that are obtained in a "Catatest(R)" as described in Example 6 are shown in Tables 5 and 6, on the one hand with alumina gel by itself and, on the other hand, with zinc aluminate.

TABLE 5

Methanolysis of Colza Oil with Alumina Calcined By Itself.

| T (° C.) | VVH | R H/A vol/vol | P (bar) | TG (%) | DG (%) | MG (%) | E (%) | t de contact (min) |
|---|---|---|---|---|---|---|---|---|
| 220 | 1 | 0.5 | 50 | 15.5 | 9.7 | 4.66 | 69.9 | 40 |
| 220 | 0.5 | 1 | 50 | 18.2 | 11.2 | 5.1 | 65.3 | 60 |
| 220 | 0.5 | 2 | 50 | 13.3 | 7.8 | 6.77 | 72.9 | 80 |
| 230 | 0.5 | 2 | 50 | 13.2 | 7.6 | 6.5 | 73.5 | 80 |
| 230 | 0.5 | 1 | 50 | 9.4 | 6.0 | 4.5 | 79.9 | 60 |
| 235 | 0.5 | 1 | 50 | 9.3 | 5.2 | 4.1 | 81.2 | 60 |

TABLE 5-continued

Methanolysis of Colza Oil with Alumina Calcined By Itself.

| T (° C.) | VVH | R H/A vol/vol | P (bar) | TG (%) | DG (%) | MG (%) | E (%) | t de contact (min) |
|---|---|---|---|---|---|---|---|---|
| 235 | 0.5 | 1 | 50 | 9.6 | 5.5 | 4.4 | 80.4 | 60 |
| 235 | 0.5 | 0.5 | 50 | 8.4 | 5.6 | 4.4 | 81.4 | 40 |
| 235 | 0.5 | 0.5 | 50 | 7.0 | 4.6 | 4.2 | 84.1 | 40 |
| 240 | 0.5 | 1 | 50 | 6.1 | 4.6 | 5.1 | 83.9 | 60 |
| 240 | 0.5 | 0.5 | 50 | 4.8 | 3.8 | 3.6 | 87.6 | 40 |
| 245 | 0.5 | 0.5 | 50 | 4.1 | 3.3 | 3.8 | 88.6 | 40 |

[Key:]
t de contact (min) = contact time (min)

TABLE 6

Methanolysis of Colza Oil on alumina + ZnO

| T (° C.) | VVH | R H/A vol/vol | P (bar) | TG (%) | DG (%) | MG (%) | E (%) | t de contact (min) |
|---|---|---|---|---|---|---|---|---|
| 230 | 0.5 | 1 | 50 | 0.3 | 1.1 | 3.9 | 94.3 | 60 |
| 230 | 0.5 | 1 | 50 | 0.2 | 1.2 | 3.9 | 94.5 | 60 |
| 240 | 0.5 | 2 | 50 | 0.02 | 1.3 | 4.35 | 94.1 | 80 |
| 240 | 0.5 | 1 | 50 | 0.23 | 1.6 | 5.3 | 92.6 | 60 |
| 240 | 0.5 | 1 | 50 | 0.13 | 1.45 | 5.2 | 93.2 | 60 |
| 235 | 0.5 | 0.5 | 50 | 0.2 | 0.95 | 5.9 | 92.9 | 40 |
| 235 | 0.5 | 0.5 | 30 | 0.3 | 1.4 | 4.0 | 94.1 | 40 |

[Key:]
t de contact (min) = contact time (min)

An increase in the conversion rate, generally at the same VVH, by 80% (with just a carrier) up to 92–95% is noted.

Thus, at 230° C., at VVH=0.5 for oil, with an oil/alcohol ratio that is equal to 1 and to 50 bar, there is 94.3% ester with zinc aluminate or the spinel and 80% with the carrier by itself. It is noted, surprisingly enough, that the carrier is much more active than the alumina-based carrier of Example 6.

Examples 6 and 7 showed a substantial improvement in activity. It is still a fact that the distribution of pores is not identical, nor the surface area, which is greater for the carrier of Example 7: 230 m², instead of 146 m² for the carrier of Example 6. In contrast, the pore volume of the carrier of Example 7 is only half of that of the carrier of Example 6. The two zinc catalysts are, in contrast, fairly similar in their performance.

EXAMPLE 8

The same catalyst as in Example 7 can be used to convert ethyl alcohol into ethyl ester. The alcohol also contains traces of methanol.

Table 7 below presents some results.

TABLE 7

Ethanolysis of Colza Oil with the Zinc Aluminate That Is Produced from Alumina Gel

| T (° C.) | VVH | R H/A vol/vol | P (bar) | TG (%) | DG (%) | MG (%) | E (%) | t de contact (min) |
|---|---|---|---|---|---|---|---|---|
| 250 | 0.5 | 0.5 | 70 | 0.5 | 1.3 | 3.6 | 94.5 | 40 |
| 250 | 0.5 | 0.5 | 70 | 0.9 | 1.7 | 4.07 | 93.2 | 40 |
| 250 | 0.5 | 0.5 | 70 | 1.34 | 1.5 | 3.5 | 93.3 | 40 |

TABLE 7-continued

Ethanolysis of Colza Oil with the Zinc Aluminate That Is Produced from Alumina Gel

| T (° C.) | VVH | R H/A vol/vol | P (bar) | TG (%) | DG (%) | MG (%) | E (%) | t de contact (min) |
|---|---|---|---|---|---|---|---|---|
| 235 | 0.5 | 0.5 | 70 | 1.5 | 2.05 | 4.1 | 92.2 | 40 |
| 240 | 0.25 | 1 | 60 | 0.01 | 0.2 | 3.4 | 96.3 | 120 |

[Key:]
t de contact (min) = contact time (min)

EXAMPLE 9

The same catalyst as in Example 6 can be used for ethanolysis of colza oil. It is noted that the presence of methanol in the ethanol promotes the reaction.

The ethanolysis of the colza oil is carried out with various methanol contents.

The operation is performed under the following conditions:

The ethanol has 370 ppm of water

VVH=0.5

T=240° C.

R H/A=1/2 vol/vol

TABLE 8

| Methanol (%) | Ethyl esters (%) |
|---|---|
| 1 | 83.4 |
| 3 | 89.3 |
| 5 | 89.2 |
| 10 | 89.7 |

EXAMPLE 10

The products that are obtained after the alcohol is evaporated are ester and glycerine. By recycling the converted esters between 70 and 90%, i.e., 82% on average and by passing them a second time over the same catalyst, the following results are obtained. The starting composition is as follows:

TG=6.9%, DG=4.5%, MG=6.9%, E=81.6%

TABLE 9

| T (° C.) | VVH | R H/A vol/vol | P (bar) | TG (%) | DG (%) | MG (%) | E (%) | t de contact (min) |
|---|---|---|---|---|---|---|---|---|
| 235 | 1 | 7 | 50 | 1.87 | 4.5 | 5.4 | 88 | 52 |
| 235 | 1 | 4 | 50 | 0.5 | 2.0 | 2.7 | 94.5 | 48 |
| 235 | 1 | 2 | 50 | 0.08 | 1.2 | 1.6 | 97.0 | 40 |

[Key:]
t de contact (min) = contact time (min)

EXAMPLE 11

The products that are obtained in a certain number of tests at between 230 and 240° C. are subjected to evaporation in a rotary evaporator to eliminate the methanol. A glycerine phase is decanted, which is most often colorless. This glycerine is treated on carbon and activated earth.

It has the following characteristics:

Coloration under cold conditions: colorless

Coloration under hot conditions at 200° C.: slightly yellow

Acidity: not detectable

Odor: none

EXAMPLE 12

In this example, a certain deactivation of the zinc oxide that is used in a device as described in Example 6 is noted.

A commercial catalyst is used that consists of spherules of pure ZnO is sold by Bayer under the description "Zink Oxide aktiv".

TABLE 10

| t (jour) | T (° C.) | P (bar) | H (cm³) | A (cm³) | t de contact (min) | VVH | TG (%) | DG (%) | MG (%) | E (%) |
|---|---|---|---|---|---|---|---|---|---|---|
| 1 | 235 | 50 | 35 | 70 | 40 | 0.5 | 0.7 | 1.8 | 3.9 | 93.6 |
| 2 | 235 | 50 | 35 | 70 | 40 | 0.5 | 5.2 | 4.7 | 5 | 85.1 |
| 8 | 240 | 50 | 35 | 70 | 40 | 0.5 | 21.5 | 15.9 | 6.9 | 55.6 |
| 10 | 240 | 50 | 35 | 70 | 40 | 0.5 | 18.8 | 17.6 | 6.1 | 56.9 |
| 3 | 235 | 50 | 70 | 70 | 30 | 1 | 29.2 | 17.4 | 5.7 | 47.5 |
| 4 | 240 | 50 | 70 | 70 | 30 | 1 | 32.1 | 18.4 | 5.6 | 43.7 |
| 13 | 240 | 50 | 70 | 70 | 30 | 1 | 33.8 | 22.2 | 7.5 | 35.7 |
| 5 | 240 | 50 | 70 | 35 | 40 | 1 | 35.3 | 21.5 | 5.8 | 37.2 |
| 14 | 240 | 50 | 70 | 35 | 40 | 1 | 42 | 21.6 | 5.8 | 30.9 |

[Key:]
t (jour) = time (day)
t de contact (min) = contact time (min)

It is noted that there is deactivation of the catalyst with pure zinc oxide.

EXAMPLE 13

In this example, it is shown that, even under purely thermal conditions, 80% conversion with a fixed bed that consists of silicon carbide, i.e., Carborundum, is obtained continuously.

TABLE 11

| T (° C.) | Débit A (cm³) | Débit H (cm³) | P (bar) | TG (%) | DG (%) | MG (%) | E (%) | t de contact (min) |
|---|---|---|---|---|---|---|---|---|
| 210 | 35 | 17.5 | 50 | 57.2 | 22.5 | 4.9 | 14.6 | 80 |
| 210 | 17.5 | 8.75 | 50 | 49.8 | 22.6 | 5.6 | 21.4 | 160 |
| 220 | 17.5 | 8.75 | 50 | 31.5 | 25.9 | 9.7 | 32.2 | 160 |
| 220 | 17.5 | 8.75 | 50 | 29.1 | 26 | 10.5 | 33.8 | 160 |
| 220 | 70 | 35 | 70 | 57.5 | 24.2 | 4.25 | 13.3 | 40 |
| 220 | 35 | 17.5 | 50 | 39.4 | 28.3 | 8.1 | 23.4 | 80 |
| 230 | 35 | 17.5 | 50 | 27.1 | 23.7 | 10.8 | 37.5 | 80 |
| 230 | 17.5 | 8.75 | 50 | 7.1 | 10.3 | 10.9 | 71.1 | 160 |
| 240 | 17.5 | 8.75 | 50 | 3.9 | 6.3 | 8.5 | 80.7 | 160 |
| 240 | 17.5 | 8.75 | 50 | 4.55 | 6.3 | 8.1 | 80.5 | 160 |
| 240 | 70 | 35 | 70 | 76.2 | 15.8 | 1.5 | 5.8 | 40 |
| 240 | 70 | 35 | 50 | 67.9 | 20.7 | 2.4 | 8.4 | 40 |
| 240 | 35 | 17.5 | 50 | 36.3 | 25.5 | 9.1 | 27 | 80 |

Débit A = débit d'alcool
Débit H = débit d'huile
[Key:]
Débit = flow rate
t de contact (min) = contact time (min)
Débit A = débit d'alcool = Flow A = alcohol flow rate
Débit H = débit d'huile = Flow H = oil flow rate A fairly high sensitivity to temperature and to contact time is noted.

EXAMPLE 14

Preparation of the Vegetable Oil Feedstock

A feedstock of 90 g of colza oil is mixed with 10 g of oleic acid, 10 g of glycerine, and 3 g of zinc oxide. It is heated in a flask that is equipped with a condenser under light boiling of nitrogen at 215° C. After 1 hour, the acidity of the oil declined from the starting theoretical value of 18 to the value of 9.4. After 3 hours, the acid number is 3, and there is only a single phase under ambient conditions, from zinc oxide. A slight amount of soap is noted to form, however.

EXAMPLE 15

Quick Purification of an Ester

A distillation of the ester phase that is obtained after one passage is carried out. After the methanol has been eliminated, the glycerine is decanted, and the ester having a purity of above 99.8%, as determined by GPC, is distilled.

The preceding examples can be repeated with similar success by substituting the generically or specifically described reactants and/or operating conditions of this invention for those used in the preceding examples.

The entire disclosure of all applications, patents and publications, cited above, and of corresponding French application No. 96/10102, are hereby incorporated by reference.

From the foregoing description, one skilled in the art can easily ascertain the essential characteristics of this invention, and without departing from the spirit and scope thereof, can make various changes and modifications of this invention to adapt it to various usages and conditions.

We claim:

1. Process for the production of at least one fatty acid ester and glycerine, characterized in that it comprises
    the reaction of a vegetable or animal oil with an aliphatic monoalcohol that contains 1 to 18 carbon atoms, in the presence of at least one catalyst comprising a mixture of zinc oxide, aluminum oxide, and zinc aluminates that corresponds to the formula: $ZnAl_2O_4$, x ZnO, y $Al_2O_3$, where each of x and y are each between 0 and 2, and wherein at least 10% of total ZnO is in the form of $ZnAl_2O_4$;
    the elimination of substantially all excess monoalcohol; and
    the separation of the fatty acid ester from glycerine.

2. A process according to claim 1, wherein said aliphatic monoalcohol contains 1 to 5 carbon atoms.

3. A process according to claim 1, wherein said catalyst comprises a zinc spinel or zinc aluminate, and the operation is carried out at a temperature of between 170° C. and 250° C., at a pressure of less than 100 bar, and with excess monoalcohol relative to oil/alcohol stoichiometry.

4. A process according to claim 1, wherein said catalyst comprises an zinc oxide in the form of powder, extrudates, or balls and the operation is carried out at a temperature of between 170 and 250° C., at a pressure of less than 100 bar, and with excess monoalcohol relative to oil/alcohol stoichiometry.

5. A process according to claim 1, wherein the catalyst has a surface area of 10 to 200 m²/g, a pore volume of 0.2 to 1.2 cm³/g, and a pore distribution of between 0.01 and 0.1 micron.

6. A process according to claim 5, wherein the catalyst has a surface area of 50 to 200 m2/g and a pore volume that is greater than 0.3 cm3/g.

7. A process according to claim 1, wherein the reaction is employed discontinuously.

8. A process according to claim 1, wherein the reaction is employed continuously, either in a fixed bed or with serial autoclaves and decanters.

9. A process according to claim 8, wherein the reaction is employed in a fixed bed, with VVH of 0.3 to 3.

10. A process according to claim 1, comprising the following successive steps:
    (a) conducting an initial transesterification with at least 80–85% conversion of the oil into fatty acid ester;
    (b) evaporating and recovering excess monoalcohol;
    (c) decanting resultant glycerine and ester mixture, wherein said ester mixture comprises fatty acid esters and unreacted or partially reacted oil;
    (d) said ester mixture being separated from said glycerine and recycled into a second stage transesterification between a portion of the monoalcohol that is recovered in step (b) and unreacted or partially reacted oil in said ester mixture; and
    (e) re-evaporating the excess monoalcohol from the second transesterification step, and decanting and separating the resultant glycerine and the fatty acid ester.

11. A process according to claim 1, wherein the starting oil is an acidic oil, and a preliminary glycerolysis operation is conducted to obtain with a catalyst used for the transesterification, free fatty acid at a temperature of between 180 and 220° C. and at a pressure of equal to or less than 1 bar.

12. A process according to claim 1, wherein the ester that is obtained is purified by being passed over a resin, an adsorbent earth, and/or active carbon.

13. A process according to claim 1, wherein the resultant ester is purified either by distillation or by washing with methanol glycerine to reduce the monoglyceride content.

14. A process according to claim 1, wherein to produce the ethyl ester, ethyl alcohol is mixed with a proportion of 1 to 50% of methanol is used.

15. A process according to claim 1, wherein the glycerine that is obtained after evaporation of the alcohol undergoes final purification by being passed over a resin, an adsorbent earth, and/or active carbon.

16. A fuel ester obtained by a process according to claim 1, containing a sterol ester content of less than 0.2% and a monoglyceride content of 0.5–5% and being essentially free of diglycerides and trigylcerides.

17. A glycerine obtained by a process according to claim 1, having a purity of greater than 99.5%.

18. A process according to claim 9, wherein the reaction is conducted at a VVH of 0.5 to 2.

19. A process according to claim 1, wherein the glycerine obtained has a purity of greater than 99.5%.

20. A process according to claim 1, wherein at least 20% of total ZnO is in the form of $ZnAl_2O_4$.

21. A process according to claim 1, wherein at least 30% of total ZnO is in the form of $ZnAl_2O_4$.

* * * * *